US009067086B2

(12) United States Patent
Danford

(10) Patent No.: US 9,067,086 B2
(45) Date of Patent: Jun. 30, 2015

(54) HIGH PERFORMANCE VENTILATORY TRAINING MASK INCORPORATING MULTIPLE AND ADJUSTABLE AIR ADMITTANCE VALVES FOR REPLICATING VARIOUS ENCOUNTERED ALTITUDE RESISTANCES

(71) Applicant: Casey J. Danford, Cadillac, MI (US)

(72) Inventor: Casey J. Danford, Cadillac, MI (US)

( * ) Notice: Subject to any disclaimer, the term of this patent is extended or adjusted under 35 U.S.C. 154(b) by 249 days.

(21) Appl. No.: 13/662,907

(22) Filed: Oct. 29, 2012

(65) Prior Publication Data

US 2013/0319420 A1    Dec. 5, 2013

Related U.S. Application Data

(63) Continuation-in-part of application No. 13/154,654, filed on Jun. 7, 2011, now Pat. No. 8,590,533.

(51) Int. Cl.
| | | |
|---|---|---|
| *A62B 18/02* | (2006.01) | |
| *A62B 18/10* | (2006.01) | |
| *A62B 18/08* | (2006.01) | |
| *A63B 21/00* | (2006.01) | |
| *A63B 23/18* | (2006.01) | |
| *A61M 16/08* | (2006.01) | |
| *A63B 21/008* | (2006.01) | |
| *A62B 9/02* | (2006.01) | |
| *A63B 69/00* | (2006.01) | |
| *A61M 16/06* | (2006.01) | |
| *A61M 16/20* | (2006.01) | |

(52) U.S. Cl.
CPC ............. *A62B 18/10* (2013.01); *A62B 18/02* (2013.01); *A62B 18/084* (2013.01); *A62B 9/02* (2013.01); *A63B 69/0028* (2013.01); *A63B 21/0004* (2013.01); *A61M 16/0683* (2013.01); *A61M 16/208* (2013.01); *A63B 21/1407* (2013.01); *A63B 23/18* (2013.01); *A61M 2202/0208* (2013.01); *A63B 2213/005* (2013.01); *A63B 21/00065* (2013.01); *A63B 21/00061* (2013.01); *A61M 16/0866* (2014.02); *A63B 21/0085* (2013.01)

(58) Field of Classification Search
CPC .................... A61M 16/0866; A61M 16/0683; A61M 16/208; A62B 18/10; A62B 18/02; A62B 18/84; A63B 23/18; A63B 21/0085; A63B 21/00065; A63B 21/00061; A63B 69/0028; A63B 2213/005
USPC ................. 137/269.5; 251/331, 335, 61–61.5
See application file for complete search history.

(56) References Cited

U.S. PATENT DOCUMENTS

| | | | |
|---|---|---|---|
| 938,247 A | * | 10/1909 | Kuhn ....................... 128/206.26 |
| 3,850,171 A | | 11/1974 | Ball et al. |
| 4,221,381 A | | 9/1980 | Ericson |
| 4,549,543 A | | 10/1985 | Moon |

(Continued)

*Primary Examiner* — Justine Yu
*Assistant Examiner* — Timothy Stanis
(74) *Attorney, Agent, or Firm* — Douglas S. Bishop

(57) ABSTRACT

A wearable training mask providing varied inhalation resistance settings and including a depth defining and air impermeable body having an exterior surface and an interior surface exhibiting a perimeter extending seal such that the body is adapted to overlay a wearer's mouth and nose. A plurality of air admittance valve subassemblies are provided and incorporated into locations along the body. Each of the valve subassemblies exhibit multiple resistance settings for affecting a degree of air flow into the mask in response to inhalation by the wearer. Straps extending from said body have interengaging ends affixing about the wearers head.

17 Claims, 5 Drawing Sheets

(56) References Cited

U.S. PATENT DOCUMENTS

| | | | |
|---|---|---|---|
| 4,601,465 A * | 7/1986 | Roy | 482/13 |
| 4,739,987 A | 4/1988 | Nicholson | |
| 4,770,413 A * | 9/1988 | Green | 482/13 |
| 4,973,047 A | 11/1990 | Norell | |
| 5,848,589 A * | 12/1998 | Welnetz | 128/200.24 |
| 6,471,621 B2 | 10/2002 | Horstel et al. | |
| 6,554,746 B1 | 4/2003 | McConnell et al. | |
| 2002/0162556 A1 * | 11/2002 | Smith et al. | 128/207.12 |
| 2004/0146842 A1 | 7/2004 | Carlucci et al. | |
| 2008/0178884 A1 * | 7/2008 | Gerson et al. | 128/206.15 |
| 2010/0101584 A1 * | 4/2010 | Bledstein et al. | 128/863 |
| 2011/0212811 A1 * | 9/2011 | Rutten | 482/13 |

\* cited by examiner

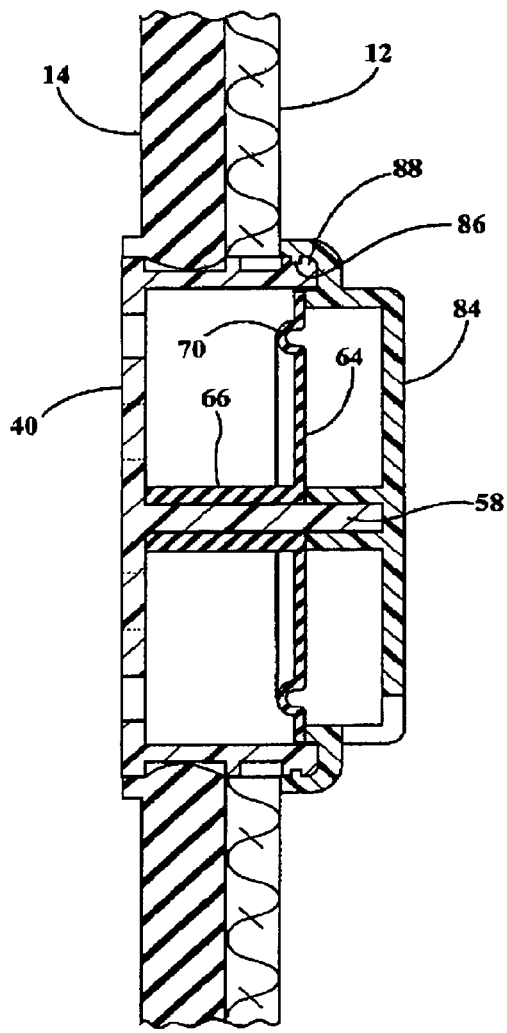 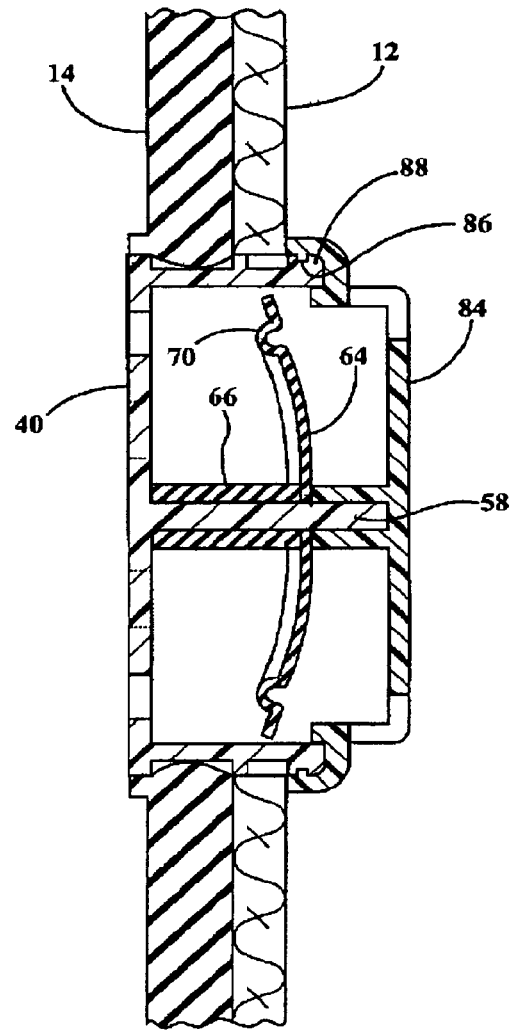
FIG. 5  FIG. 6

HIGH PERFORMANCE VENTILATORY TRAINING MASK INCORPORATING MULTIPLE AND ADJUSTABLE AIR ADMITTANCE VALVES FOR REPLICATING VARIOUS ENCOUNTERED ALTITUDE RESISTANCES

CROSS-REFERENCE TO RELATED APPLICATIONS

The present application is a continuation in part of U.S. Ser. No. 13/154,654, filed Jun. 7, 2011.

FIELD OF THE INVENTION

The present invention rotates generally to air inhalation resistance devices, such as utilized in the field of exercise and extreme sports. More specifically, the present invention discloses a high performance and hands free wearable ventilatory training mask which incorporates multiple and adjustable air admittance valves for replicating various encountered altitude resistances.

BACKGROUND OF THE INVENTION

As is known with human physiology, the two phases of ventilation include inhalation (air moving into the lungs) and expiration (air leaving the lungs). The scientific principle governing such aspects of inhalation is known as Boyle's law which operates under the principle that air moves from areas of high to low pressure.

Inspiratory muscle exercising and training devices are known and which operate under the principle of limiting air intake during inhalation, the result of width assists in developing lung function and capacity through the development of the muscles responsible for assisting inhalation. Primary among these are the diaphragm and external intercostal muscle groups which operate to expand the space in the rib cage downward (diaphragm) and enlarge the rib cage outward (intercostals).

Accessory muscles, such as including the scalenes, latismus dorsi, pec major-minor, and others are additionally provided and operate to varying deuces depending upon a level of fatigue or limited expulsion experienced with the primary muscle groups. A common occurrence among individuals is when the primary muscle groups are relatively weak in comparison to these and other secondary/accessory muscles and such that the individual is not experiencing maximum lung expansion during exercise, along with experiencing other undesirable side effects including cramping and chest tightness.

One example of an inspiratory muscle training device is depicted in U.S. Pat. No. 6,554,746, to McConnell and when includes a chamber having an opening for the passage of air to be inhaled and exhaled, along with an inlet permitting air to be inhaled to enter the chamber and to pass to the opening. A one-way exhaust valve permits exhaled air entering through the opening to escape from the chamber, and another valve is provided to resist the entry of air to be inhaled into the chamber. The latter valve serves to vary the degree of resistance in dependence upon the volume of air that has passed through the inlet.

Additional examples respiratory exercise devices include the therapeutic device of Norell, U.S. Pat. No. 4,973,047, the device of Carlucci U.S. 2004/0146842, and the devices respectively shown in each of Ericson U.S. Pat. No. 4,221,381 (Ericson) and U.S. Pat. No. 4,739,987 (Nicholson).

SUMMARY OF THE INVENTION

The present invention discloses a high performance and hands free wearable ventilator training mask which incorporates a plurality of adjustable air admittance valves for replicating various encountered altitude resistances, by adjusting an inhalation resistance setting corresponding to a given altitude, and which operates to assist the wearer in developing the various muscle primary and secondary muscle groups employed in breathing. The ventilator training mask exhibits a depth defining and air impermeable body with an exterior surface and an interior surface exhibiting a perimeter extending seal, such that the body is adapted to overlay a wearer's mouth and nose. The body further has a two layer construction including an outer fabric layer overlaying an inner rubberized layer integrating said perimeter extending seal.

A plurality, typically first, second and third, of air admittance valve subassemblies are incorporated into locations along said body, each of said valve subassemblies having multiple resistance settings for affecting a degree of air flow into said mask in response to inhalation by the wearer. The valve subassemblies each include a stem supporting and air passageway configured base mounted through the body in communication with the exterior and interior surfaces.

A flexible diaphragm is mounted to the stem in seating fashion within the base, a cap engaging upon an exterior side of the base and through which are defined a select number air flow permitting apertures. Each of the diaphragms has a thin and substantially planar shape portion exhibiting an outline matching an inner facing perimeter of the base. A post exhibiting a channeled interior extends from the planar shape portion and mounts over the supporting stem for arraying the planar portion within the base.

The diaphragm can be reversibly mounted to the stem between a first position in which the outer planar shape portion extends radially at an elevated location within the base in an inhalation permitting configuration, and a second position in which the planar shape overlays the passageway configured base in a substantially inhalation preventing configuration. The interchangeable caps each further exhibit an outer circumferential extending portion and an inner raised portion incorporating a selected number of apertures for establishing the inhalation resistance setting.

Straps extending from said body and having inter-engaging ends for affixing about the wearers head. The straps each further comprising interior cutout configurations for seating around and behind the wearer's ears, along with opposite end disposed and inter-engageable hook and loop fasteners.

BRIEF DESCRIPTION OF THE DRAWINGS

Reference will now be made to the attached drawings, when read in combination with the following detailed description, wherein like reference numerals refer to like parts throughout the several views, and in which:

FIG. 5 is a lengthwise cutaway taken along line 5-5 of FIG. 1 of a selected valve subassembly and which depicts a flexible diaphragm portion in a first sealed configuration; and FIG. 6 is a succeeding view to FIG. 5 and depicts the flexible diaphragm in an inwardly resisting and arcuate deflected condition resulting from an inhalation by the wearer.

DETAILED DESCRIPTION OF THE PREFERRED EMBODIMENTS

With reference to FIGS. 1-6, and as previously described, the present invention discloses a high performance and hands free wearable ventilatory training mask, generally at 10, according to one non-limiting variant of the present invention. As will be further described, a feature of the ventilator mask is the incorporation of multiple and adjustable air admittance valves for replicating the inhalation properties associated with various encountered altitude resistances and to better assist the wearer, such as engaged in a training or exercise discipline, in developing lung function, muscle development and associated stamina.

Figure 1:
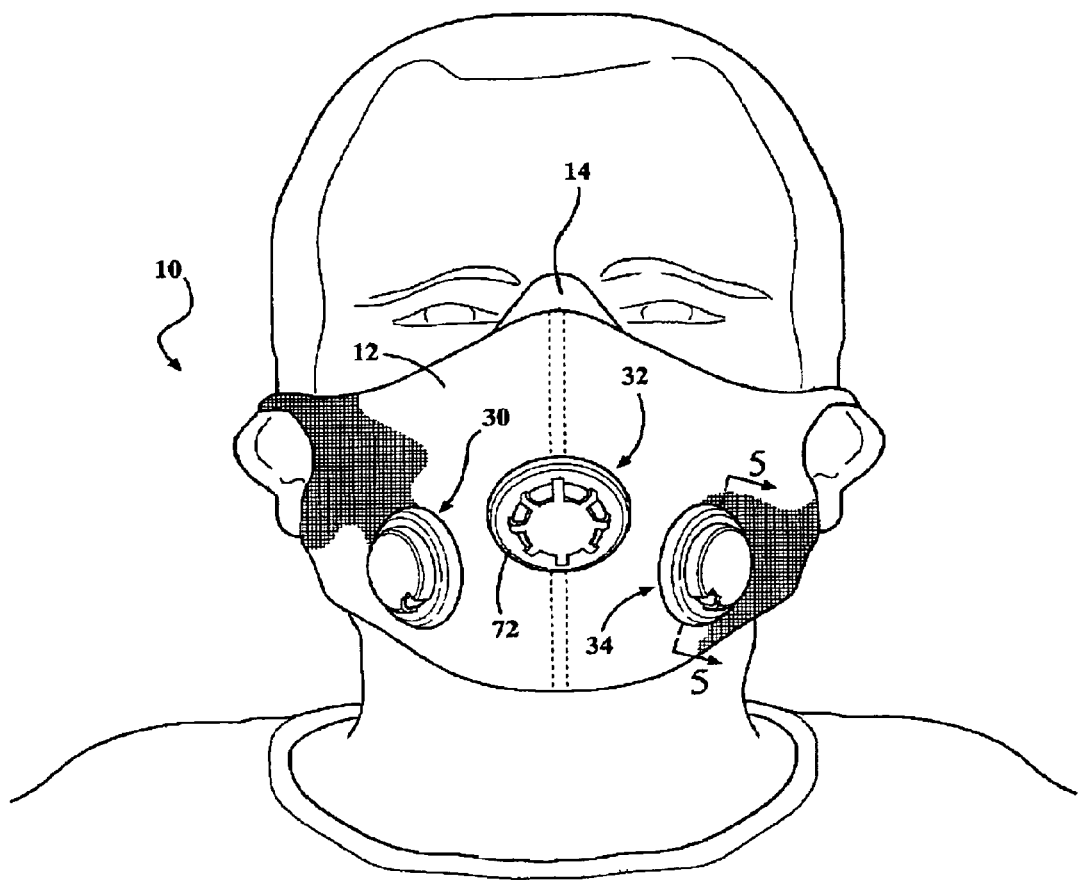
FIG. 1 is an operational view of the ventilatory training mask according to one depicted variant being worn by a user.

The ventilator training mask 10 exhibits a depth defining and air impermeable body in the form of a two layer construction including an outer fabric layer 12 overlaying an inner rubberized and enclosed perimeter defining layer 14 integrating a likewise perimeter extending seal 16 which is adapted to overlay the nose and mouth of a wearer in the fashion depicted in FIG. 1. A pair of straps are depicted as integral portions 18 and 20 of the fabric layer 12 extending from a middle location overlapping the rubberized attached layer 14, the straps 18 and 20 have inter-engaging ends 22 and 24 in the form of hook and loop fasteners for affixing the ventilatory mask 10 about the wearers head (again FIG. 1). The straps 18 and 20 each further depict interior cutout configurations, shown at 26 and 28 by inner cutout area defining surfaces, for seating around and behind the wearer's ears.

Figure 4:
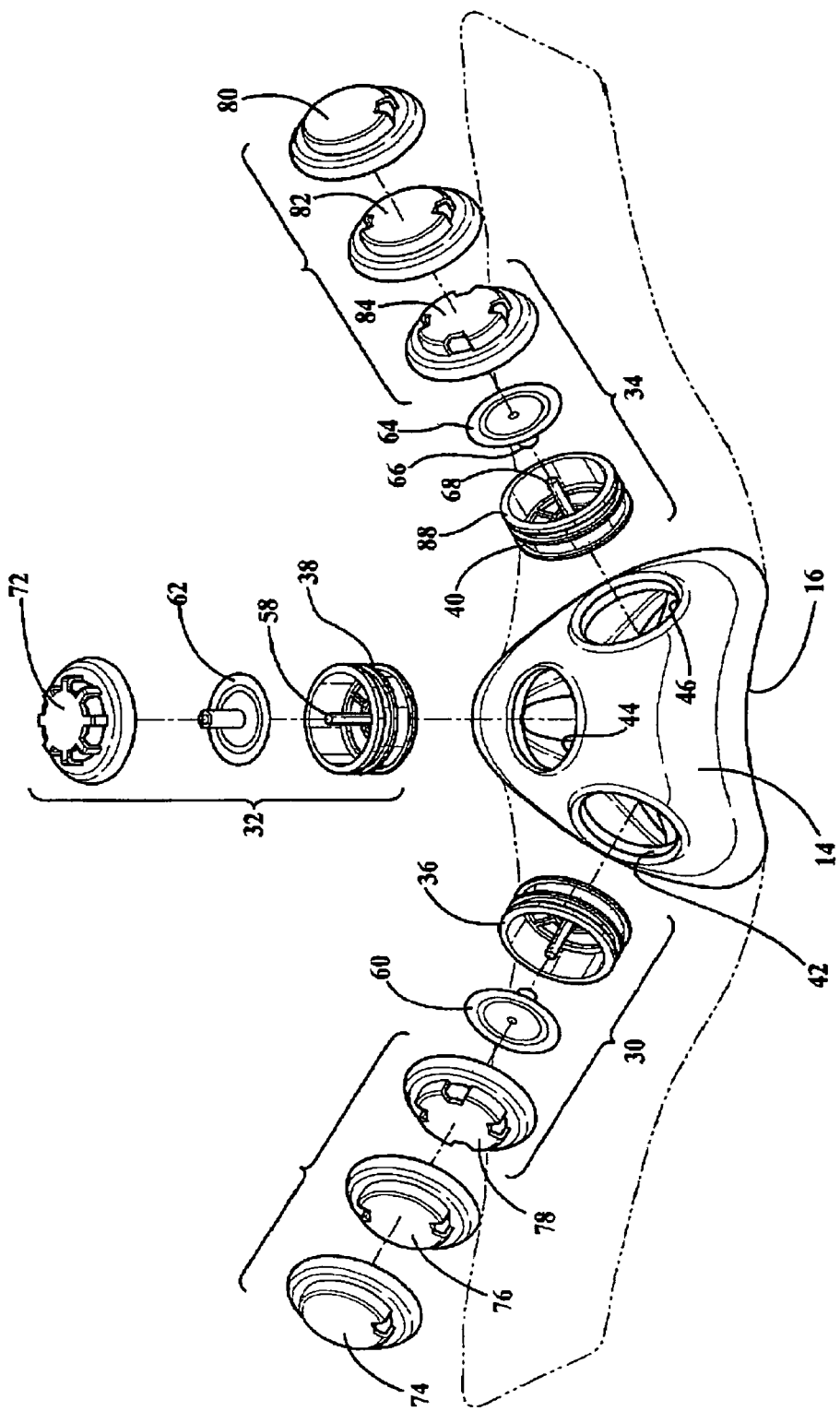
FIG. 4 is an exploded view of the training mask and the individual valve subassemblies which allow for customizing inhalation resistance in order to replicate a variety of altitude elevations.

A plurality of air admittance valve subassemblies are incorporated, such as depicted by air valve subassemblies 30, 32, and 34 as best shown in the exploded view of FIG. 4, are incorporated into locations along the body as further depicted by the rubberized and perimeter defining layer 14. Each of the valve subassemblies are constructed to provide multiple resistance settings for affecting a degree of air flow into the mask 10, this in response to inhalation by the wearer when the mask is mounted into the configuration of FIG. 1.

The valve subassemblies 30, 32 and 34 each include a stem supporting and air passageway configured base, shown at each of 36, 38 and 40 in the exploded perspective of FIG. 4, with selected base 40 further depicted in cross sectional cutaway in each of FIGS. 5 and 6. As depicted, the base 36, 38 and 40 each exhibits a desired shape such as cylindrical and which is mounted through the body, this depicted in FIG. 4 as corresponding inner extending perimeter surfaces 42, 44 and 46 associated with the rubberized inner layer 14 and so that the base components 36, 38 and 40 are in communication with the exterior and interior surfaces of the mask. Although not shown, the outer fabric layer 12, depicted in FIGS. 1-3 in mounted overlaying fashion over the inner rubberized layer 14, includes likewise aligning cutout profiles for mating with the cutout perimeter surfaces 42, 44 and 46 in FIG. 4.

Figure 3:
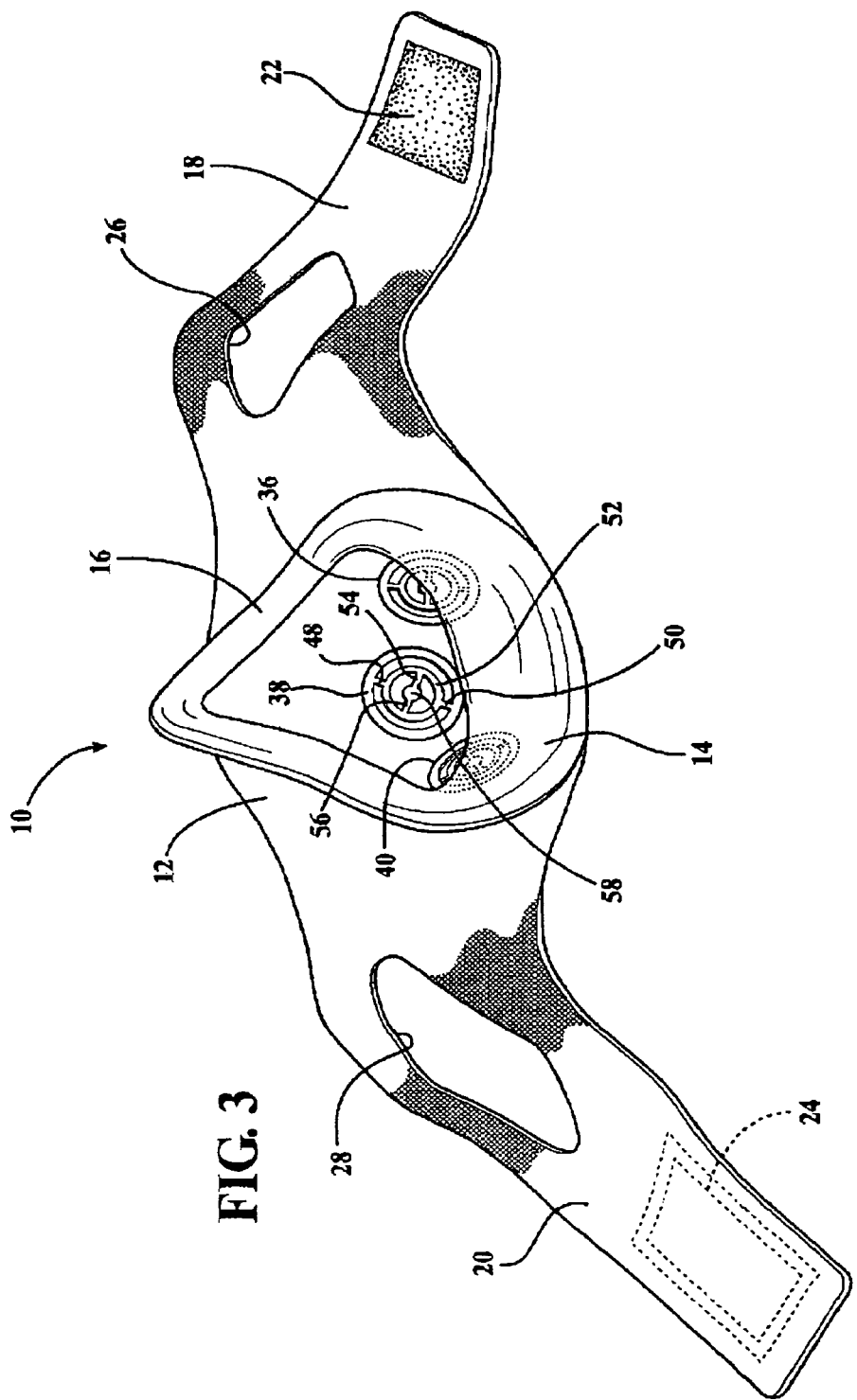
FIG. 3 is a rotated perspective of the training mask depicted in FIG. 2 and illustrating the perimeter extending and sealing profile associated with the main body for overlaying the wearer's mouth and nose in sealed fashion.

As best shown when viewing FIG. 4 in combination with the reversed perspective of FIG. 3, each base 16, 38 and 40 (and with reference specifically to selected base 38) exhibits a webbed configuration for facilitating easy air flow through the base (absent a determined inhalation resistance setting to be described below). As further shown, this includes in one non-limiting configuration a bottom layer of the base (again referencing selected base 38) as having a plurality of interconnecting portions including outer web locations 48 and 50, an inner arcuate supported web 52, and inner-most web locations 54 and 56 which collectively establish the desired air flow permeability combined with supporting, at an innermost central location, an outwardly extending stem 58 (see again FIG. 4).

A plurality of flexible diaphragms are shown at each of 60, 62 and 64 in FIG. 4 and are each mounted to an associated stem in seating fashion within the associated base 36, 38 and 40. As further best shown in FIG. 4, in combination with the linear cutaways of FIGS. 5 and 6, each of the diaphragms, with reference in particular to selected diaphragm 64 associated with middle (second) valve subassembly 32, are each constructed of a rubberized or deformable material which includes a thin and substantially planar shape portion exhibiting an outline matching an inner facing perimeter of the associated base. A post, best shown at 66 for selected diaphragm 64, exhibits a channeled interior extending from the outer and thin planar shape portion and which mounts over the corresponding supporting stem (at 68 in FIG. 4) for arraying the planar portion of the diaphragm within the base 40.

In this fashion, and referencing first the cutaway of FIG. 5, the selected flexible diaphragm is depicted in each of a first sealed configuration in which an out ribbed and perimeter extending location 70 is depicted in an un-deflected condition. With further reference to FIG. 6, the flexible diaphragm is depicted in an inwardly resisting responsive and arcuate deflected condition such as which results from inhalation inducted by the wearer.

As shown in FIG. 4, it is understood that any one or more of the diaphragms 60, 62, and 66 can be reversibly mounted (as depicted by middle selected diaphragm 62) to the corresponding base extending stem 58). In this manner, the other selected pair of diaphragms 60 and 64 are arranged in the first position depicted in FIGS. 5 and 6, and again in which the outer planar shape portion extends radially at an elevated location within the base in an inhalation permitting configuration with the middle diaphragm 62 being arranged in a second position in which the planar shape overlays closely the bottom surface of the webbed constructed and airflow passageway configured base, such as further providing the selected valve subassembly with a substantially inhalation preventing configuration. In this fashion, the positioning of the diaphragm 60, 62 and/or 64 establishes one variable (along with the cap configuration to be described below) for establishing a desired degree of inhalation airflow resistance within the overall ventilatory mask.

Figure 2:
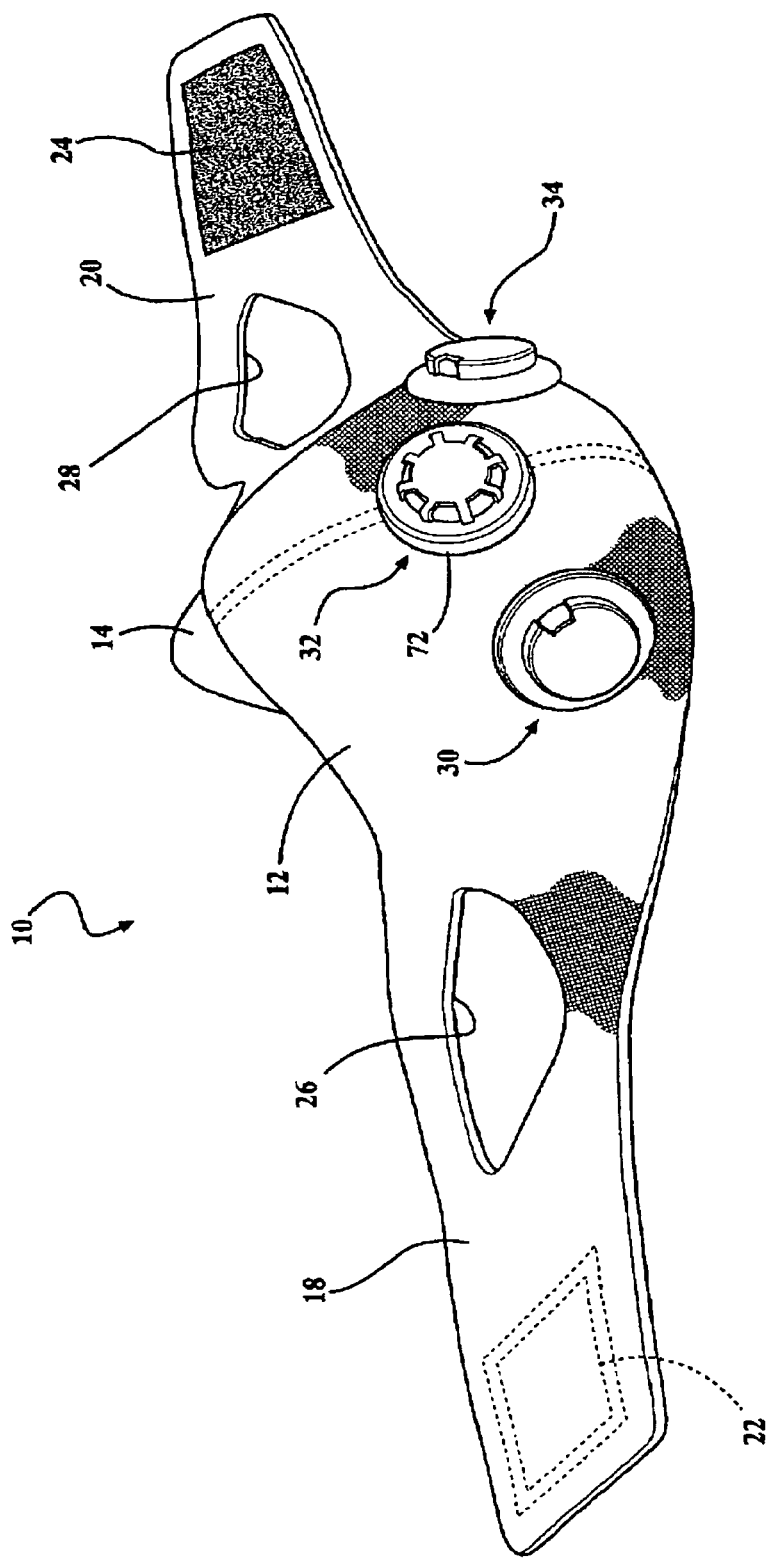
FIG. 2 is a detached perspective of the training mask and which better depicts the integrally formed straps extending from the three dimensional and mouth and nose overlaying body, the straps further including interior cutout configurations for seating around and behind the wearer's ears, along with opposite end disposed anti inter-engageable hook and loop fasteners.

Each of the valve subassemblies further includes one or more exterior engageable caps, and such as which are depicted by a single cap 72 attachable over an exterior rim of middle defined base 58 of valve subassembly 32 in each of FIGS. 1, 2 and 4. As further shown in exploded FIG. 4, plural alternatively engageable caps are depicted respectively at 74, 76 and 78 for valve subassembly 30, with a like plurality of alternatively engageable caps depicted at 80, 82 and 84 for further selected valve subassembly 34.

Each of the caps 72-84 engages upon an exterior side of its associated base (this further best shown by selected cap 84 in the cutaway of FIGS. 5-6 which includes an outer most perimeter located and inwardly facing edge profile 86 for engaging underneath an outermost lip edge (at 88 of the selected base 40. Each of the caps 72-84 further exhibits an outer circumferential extending portion and an inner raised portion incorporating a selected number of apertures defined about a perimeter thereof and for establishing (to some degree along with the positioning of the associated diaphragm) the inhalation resistance setting associated with the given valve subassembly.

As depicted, the number of airflow permitting apertures configured in the alternately engageable caps can vary from a single such aperture, shown in selected caps 74 and 80 in FIG. 4, a pair of apertures as depicted in further selected caps 76 and 82, a larger number (by example four) of apertures in further selected caps 78 and 84, up to a largest number of flow permitting apertures associated with further selected (middle valve attaching) cap 72. The potential configuration of the caps are not limited by those depicted at each of 72-84 and it is further envisioned that additional configurations can include such as caps with no apertures (thus effectively cutting of inhalation or exhalation flow) associated with a given subassembly.

Although not shown, it is also envisioned that any one or more of the caps can include multiple and circumferentially inter-adjustable layers which may allow for adjusting a level of inhalation resistance without the need for interchanging one cap for another. The valve assemblies can be further configured to provide any degree of exhalation freedom or resistance, depending upon the desired variables for establishing a given respiratory training regimen and which is consistent with the above description.

Accordingly, the training mask provides a variety of altitude mimicking aspects for increasing inhalation resistance, such as which enhances the effectiveness of any training or exercise regimen. In particular, the elevation training mask provides for strengthening the diaphragm and sculpts abdominal muscles, conditioning the lungs by creating desired levels of pulmonary resistance, increasing the surface area and elasticity in the alveoli, increasing both lung capacity and oxygen processing efficiency, and likewise increasing anaerobic thresholds.

Having described my invention, other and additional preferred embodiments will become apparent to those skilled in the art to which it pertains, and without deviating from the scope of the appended claims.

I claim:

1. A wearable training mask providing variable inhalation resistance settings, comprising:
    a depth defining and air impermeable body having an exterior surface and an interior surface exhibiting a perimeter extending seal such that said body is adapted to overlay a wearer's mouth and nose;
    a plurality of air admittance valve subassemblies incorporated into locations along said body, each of said valve subassemblies having multiple resistance settings for affecting a degree of air flow into said mask in response to inhalation by the wearer;
    said valve subassemblies each further having a stem support an air passageway configured base mounted through said body in communication with said exterior and interior surfaces;
    a flexible diaphragm mounting to said stem within said base, a cap engaging upon an exterior side of said base and through which are defined a select number of air flow permitting apertures;
    said diaphragm having a thin and substantially planar shape portion exhibiting an outline matching an inner facing perimeter of said base, a post exhibiting a channeled interior and extending from said planar shape portion and mounting over said supporting stem for arraying said planar portion within said base; and
    straps extending from said body and having inter-engaging ends adapted for affixing about the wearers head.

2. The training mask as described in claim 1, further comprising a plurality of interchangeable caps exhibiting different configurations of air flow permitting apertures.

3. The training mask as described in claim 2, said interchangeable caps each further comprising an outer circumferential extending portion and an inner raised portion incorporating a selected number of apertures for establishing the inhalation resistance setting.

4. The training mask as described in claim 1, farther comprising said diaphragm being reversibly mounted to said stem between a first position in which said planar shape extends radially at an elevated location within said base in an inhalation permitting configuration and a second position in which said planar shape overlays said passageway configured base in as substantially inhalation preventing configuration.

5. The training mask as described in claim 1, said straps each farther comprising interior cutout configurations for seating around and behind the wearer's ears, along with opposite end disposed and inter-engageable hook and loop fasteners.

6. The training mask as described in claim 1, said body further comprising a two layer construction including an outer fabric layer overlaying an inner rubberized layer integrating said perimeter extending seal.

7. The training mask as described in claim 1, farther comprising first, second and third individual valve subassemblies.

8. A wearable training mask providing variable inhalation resistance settings, comprising:
    a depth defining and air impermeable body having an exterior surface and an interior surface exhibiting a perimeter extending seal such that said body is adapted to overlay a wearer's mouth and nose;
    at least one air admittance valve subassembly incorporated into at least one location along the body, the valve subassembly having a stem support an air passageway configured base mounted through said body in communication with said exterior and interior surfaces;
    a flexible diaphragm mounting to said stem within said base, at least one cap interchangeably engaging upon an exterior side of said base and through which are defined a select number of air flow permitting apertures for establishing a selected resistance setting for affecting a degree of air flow into said mask in response to inhalation by the wearer;
    said diaphragm having a thin and substantially planar shape portion exhibiting an outline matching an inner facing perimeter of said base, a post exhibiting a channeled interior and extending from said planar shape portion and mounting over said supporting stem for arraying said planar portion within said base; and
    straps extending from said body and having inter-engaging ends adapted for affixing about the wearers head.

9. The training mask as described in claim 8, further comprising said diaphragm being reversibly mounted to said stem between a first position in winch said planar shape extends radially at an elevated location within said base in an inhalation permitting configuration and a second position in which said planar shape overlays said passageway configured base in a substantially inhalation preventing configuration.

10. The training mask as described in claim 8, said straps each further comprising interior cutout configurations for seating around and behind the wearer's ears, along with opposite end disposed and inter-engageable hook and loop fasteners.

11. The training mask as described in claim 8, said body further comprising a two layer construction including an outer fabric layer overlaying an inner rubberized layer integrating said perimeter extending seal.

12. The training mask as described in claim 8, further comprising first, second and third individual valve subassemblies.

13. The training mask as described in claim 8, said interchangeable caps each further comprising an outer circumferential extending portion and an inner raised portion incorporating a selected number of apertures for establishing the inhalation resistance setting.

14. A wearable training mask providing variable inhalation resistance settings, comprising:
   a depth defining and air impermeable body having a two layer construction including an outer fabric layer overlaying an inner rubberized layer integrating a perimeter extending seal such that said body is adapted to overlay a wearer's mouth and nose;
   a plurality of air admittance valve subassemblies incorporated into locations along said body, each of said valve subassemblies having multiple resistance settings for affecting a degree of air flow into said mask in response to inhalation by the wearer;
   said valve subassemblies each further having a stem support an air passageway configured base mounted through said body in communication with said exterior and interior surfaces;
   a plurality of caps, each having a number of air apertures, a selected one of said caps affixing to each base of a selected valve subassembly, such that said caps are replaceably attached to establish variable total numbers of air flow permitting apertures; and
   straps extending from said body and including interior cutout configurations adapted for seating around and behind the wearer's ears, opposite end disposed and inter-engageable hook and loop fasteners securing about the wearer's head.

15. The training mask as described in claim 14, said valve subassemblies each further comprising a stem supporting and air passageway configured base mounted through said body in communication with said exterior and interior surfaces.

16. The training mask as described in claim 15, further comprising a flexible diaphragm mounting to said stem within said base, a cap engaging upon an exterior side of said base and through which are defined a select number of air flow permitting apertures.

17. The training mask as described in claim 14, each of said caps further comprising a perimeter extending rim, an underside of which resistively fitting over an exterior perimeter end surface associated with said each base of said valve subassemblies.

* * * * *